(12) United States Patent
Boaz

(10) Patent No.: US 6,939,981 B1
(45) Date of Patent: Sep. 6, 2005

(54) RUTHENIUM COMPLEXES OF PHOSPHINE-AMINOPHOSPHINE LIGANDS

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/876,392

(22) Filed: Jun. 25, 2004

(51) Int. Cl.$^7$ .......................... C07F 15/00; B01J 31/00; C07C 31/18
(52) U.S. Cl. ..................... 556/14; 556/17; 556/21; 556/137; 502/162; 568/852; 568/862; 568/881
(58) Field of Search ................ 556/14, 17, 21, 556/137; 568/852, 862, 881; 502/162

(56) References Cited

U.S. PATENT DOCUMENTS

| | | | |
|---|---|---|---|
| 5,856,540 A * | 1/1999 | Jendralla | 556/21 |
| 6,573,389 B1 | 6/2003 | Bosch et al. | |
| 6,590,115 B2 | 7/2003 | Boaz et al. | |
| 6,777,567 B2 * | 8/2004 | Weissensteiner et al. | 556/16 |

OTHER PUBLICATIONS

Mashima et al, J. Org. Chem., 1994, 59, pp. 3064-3076.
Kitamura et al, Org. Syn., 1992, 71, pp. 1-13.
Genet et al, Tetrahedron:Asymmetry, 1991, vol. 2, No. 1, pp. 43-46.
Genet et al, Tetrahedron:Asymmetry, 1994, vol. 5, No. 4, pp. 665-674.
Genet et al, Tetrahedron:Asymmetry, 1994, vol. 5, No. 4, pp. 675-690.
Mezzetti et al, J. Chem. Soc., Chem. Commun., 1991, pp. 1675-1677.
Mezzetti et al, J. Chem. Soc. Dalton Trans., 1995, pp. 49-56.
Stoop et al, Organometallics, 1998, 17, pp. 668-675.
Maienza et al, Tetrahedron:Asymmetry, 2002, 13, pp. 1817-1824.

* cited by examiner

Primary Examiner—Porfirio Nazario-Gonzalez
(74) Attorney, Agent, or Firm—Michael J. Blake; Bernard J. Graves, Jr.

(57) ABSTRACT

Disclosed are ruthenium complexes of phosphine-aminophosphine ligands that may be used to catalyze large number of reactions of a wide variety of substrates such as asymmetric hydrogenations, asymmetric reductions, asymmetric hydroborations, asymmetric olefin isomerizations, asymmetric hydrosilations, asymmetric allylations, and asymmetric organometallic additions. Also disclosed is a process for the preparation of the ruthenium complexes and processes for the enantioselective asymmetric hydrogenations of 1,3-dicarbonyl, α-hydroxycarbonyl, and β-hydroxycarbonyl compounds to produce the corresponding hydroxycarbonyl, 1,2-diol, and 1,3-diol compounds, respectively, using the ruthenium complexes to catalyze the hydrogenation.

21 Claims, No Drawings

RUTHENIUM COMPLEXES OF PHOSPHINE-AMINOPHOSPHINE LIGANDS

FIELD OF THE INVENTION

This invention pertains to certain novel ruthenium complexes of phosphine-aminophosphine ligands and to a process for the preparation thereof. The ruthenium complexes may be used to catalyze large number of reactions of a wide variety of substrates such as asymmetric hydrogenations, asymmetric reductions, asymmetric hydroborations, asymmetric olefin isomerizations, asymmetric hydrosilations, asymmetric allylations, and asymmetric organometallic additions.

BACKGROUND OF THE INVENTION

Asymmetric catalysis is the most efficient method for generating products with high enantiomeric purity, as the asymmetry of the catalyst is multiplied many times over in generating the chiral product. These chiral products have found numerous applications as building blocks for single enantiomer pharmaceuticals as well as in some agrochemicals. The asymmetric catalysts employed can be enzymatic or synthetic in nature. The latter types of catalyst have much greater promise than the former due to much greater latitude of applicable reaction types. Synthetic asymmetric catalysts are usually composed of a metal reaction center surrounded by one or more organic ligands. The ligands usually are generated in high enantiomeric purity, and are the agents inducing the asymmetry. These ligands are in general difficult to make and therefore expensive. A notable exception are chiral phosphine-aminophosphine ligands useful as metal complexes for asymmetric catalysis which are readily prepared and air-stable, and have been described by Boaz et al. in U.S. Pat. No. 6,590,115.

The asymmetric hydrogenation of β-ketoesters to β-hydroxyesters has received significant attention, particularly as these products have a number of industrial applications, not the least of which is a synthetic intermediate in the synthesis of atorvastatin. The complexes that are used for this type of hydrogenation are largely ruthenium-based, with the most effective catalysts derived from axially chiral ligands such as BINAP. See, for example, Mashima et al. *J. Org. Chem.* 1994, 59, 3064–3076; and Kitamura, et al., *Org. Synth.* 1992, 71, 1–13. There are a number of methods to prepare ruthenium complexes of bidentate chiral ligands. These methods, many of which are multi-step, are often troublesome and not particularly general, resulting in complexes with varying hydrogenation activities and enantioselectivities. Perhaps the most versatile, general, and useful ruthenium complexes have methallyl ancillary ligands in addition to the chiral bis-phosphine. See, for example, Genet et al., *Tetrahedron:Asymm.* 1991, 2, 43–46; Genet et al., *Tetrahedron:Asymm.* 1994, 5, 665–674; and Genet et al., *Tetrahedron:Asymm.* 1994, 5, 675–690. These methallyl species are generally prepared using multistep processes with harsh reaction conditions (e.g., strong acid), which may not be compatible with phosphine-aminophosphine ligands. One of the simplest preparations of ruthenium complexes is by ligand displacement from commercially available species such as tris(triphenylphosphine)ruthenium dichloride. These preparations have generally involved the reaction of chiral bidentate bis-phosphine ligands with the latter complex and result in ruthenium dichloride complexes containing one chiral bidentate ligand and one (achiral) triphenylphosphine (Mezzetti, A.; Consiglio, G. *J. Chem. Soc., Chem. Commun.* 1991, 1675–1677.). There have been relatively few complexes prepared using this methodology, and although certain species show high enantioselectivity for 1,3-diketone hydrogenations, the hydrogenation of β-ketoester substrates has proceeded with only moderate enantioselectivity (Mezzetti, A.; Tschumper, A.; Consiglio, G. *J. Chem. Soc. Dalton Trans.* 1995, 49–56; Stoop, R. M.; Mezzetti, A.; Spindler, F. *Organometallics* 1998, 17, 668–675; Maienza, F.; Santoro, F.; Spindler, F.; Malan, C.; Mezzetti, A. *Tetrahedron: Asymm.* 2002, 13, 1817–1824.). In no cases have ruthenium complexes of phosphine-aminophosphines been prepared in this manner.

BRIEF SUMMARY OF THE INVENTION

We have discovered a series of novel, substantially enantiomerically-pure ruthenium complexes of phosphine-aminophosphine ligands. Thus, the present invention provides ruthenium complex compounds comprising a ruthenium compound having formula 1

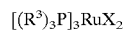

$$[(R^3)_3P]_3RuX_2 \qquad 1$$

and a chiral substantially enantiomerically pure ligand having formula 2

$$(R)_2P\text{—}L\text{—}N(R^2)P(R^1)_2 \qquad 2$$

wherein

R, $R^2$, and $R^3$ are, independently, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, and substituted or unsubstituted $C_4$–$C_{20}$ heteroaryl having one to three heteroatoms wherein the heteroatoms are selected from sulfur, nitrogen, and oxygen;

$R^1$ is substituted or unsubstituted, branched- or straight-chain $C_1$–$C_{20}$ alkyl, substituted or unsubstituted, branched- or straight-chain $C_1$–$C_{20}$ alkoxy, substituted or unsubstituted $C_3$–$C_8$ cycloalkyl, substituted or unsubstituted $C_3$–$C_8$ cycloalkoxy, substituted or unsubstituted $C_6$–$C_{20}$ carbocyclic aryl, substituted or unsubstituted $C_6$–$C_{20}$ carbocyclic aryloxy;

X is fluoride, chloride, bromide, or iodide, and

L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenylmethylene wherein L is substantially enantiomerically pure, i.e., an enantiomeric excess of 90% or greater.

The preferred complexes of our invention are those wherein $R^3$ is phenyl and $(R)_2P\text{—}L\text{—}N(R^2)P(R^1)_2$ collectively represent structure 3 or 4 (the enantiomer of 3)

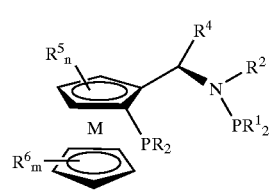

3

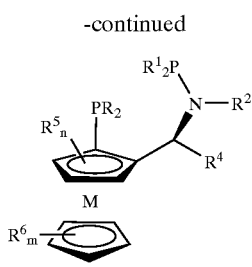

wherein

R, $R^1$, and $R^2$ are as described above;

$R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

n is 0 to 3;

m is 0 to 5; and

M is selected from the metals of Groups IVB, VB, VIIB, VIIB and VIII.

Another embodiment of the present invention is a process for preparing the novel complex compounds which comprises contacting a ruthenium compound having formula 1

$$[(R^3)_3P]_3RuX_2 \qquad 1$$

with a chiral substantially enantiomerically pure ligand having formula 2

$$(R)_2P\text{—}L\text{—}N(R^2)P(R^1)_2 \qquad 2$$

in an inert organic solvent, wherein R, $R^1$, $R^2$, $R^3$, L and X are as defined above. A further embodiment of the present invention is a process for the asymmetric hydrogenation of a 1,3-dicarbonyl compound to produce the corresponding hydroxycarbonyl compound, which comprises contacting the dicarbonyl compound with hydrogen in the presence of a ruthenium complex comprising ruthenium compound 1 and ligand 2.

The present invention also recites a process for the asymmetric hydrogenation of a hydroxycarbonyl compound to produce the corresponding diol compound which comprises contacting the hydroxycarbonyl compound with hydrogen in the presence of a ruthenium complex comprising ruthenium compound 1 and ligand 2.

DETAILED DESCRIPTION

The alkyl groups that may represent each of R, $R^1$, $R^2$, $R^3$, $R^4$, $R^5$, and $R^6$ may be straight- or branched-chain aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, hydroxy, aryl or halogen. The terms "$C_1$–$C_6$-alkoxy", "$C_2$–$C_6$-alkoxycarbonyl", and "$C_2$–$C_6$-alkanoyloxy" denote radicals corresponding to the structures —$OR^7$, —$CO_2 R^7$, and $OCOR^7$, respectively, wherein $R^7$ is $C_1$–$C_6$-alkyl or substituted $C_1$–$C_6$-alkyl. The term "$C_3$–$C_8$-cycloalkyl" denotes a saturated, carbocyclic hydrocarbon radical having three to eight carbon atoms. The aryl groups that each of R, $R^1$, $R^2$, $R^3$, $R^4$, $R^5$, and $R^6$ represent may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino or —O—$R^8$, S—$R^8$ $SO_2$—$R^8$, —$NHSO_2R^8$ or —$NHCO_2R^8$, wherein $R^8$ is phenyl, naphthyl, or phenyl or naphthyl substituted with one to three groups selected from $C_1$–$C_6$-alkyl, $C_6$–$C_{10}$ aryl, $C_1$–$C_6$-alkoxy or halogen. The heteroaryl radicals include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl or $C_2$–$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The alkoxy groups which may be represented by $R^1$ may be straight- or branched-chain aliphatic alkoxy radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, aryl and halogen. The terms "$C_1$–$C_6$-alkoxy", "$C_2$–$C_6$-alkoxycarbonyl", and "$C_2$–$C_6$-alkanoyloxy" are used to denote radicals corresponding to the structures —$OR^7$, —$CO_2 R^7$, and —$OCOR^7$, respectively, wherein $R^7$ is $C_1$–$C_6$-alkyl or substituted $C_1$–$C_6$-alkyl. The term "$C_3$–$C_8$-cycloalkoxy" denotes a saturated, carbocyclic alkoxy radical having three to eight carbon atoms. The aryloxy groups that $R^1$ represent may include phenoxy, naphthyloxy, or anthracenyloxy and phenyloxy, naphthyloxy, or anthracenyloxy substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, $C_2$–$C_6$-alkoxycarbonyl, $C_2$–$C_6$-alkanoylamino or —O—$R^8$, —$SO_2$—$R^8$, —$NHSO_2R^8$ and —$NHCO_2R^8$, wherein $R^8$ is phenyl, naphthyl, or phenyl or naphthyl substituted with one to three groups selected from $C_1$–$C_6$-alkyl, $C_6$– $C_{10}$ aryl, $C_1$–$C_6$-alkoxy or halogen. The term "halogen" is used to include fluorine, chlorine, bromine, and iodine.

The skilled artisan will understand that each of the references herein to groups or moieties having a stated range of carbon atoms, such as "$C_1$–$C_6$-alkyl," includes not only the $C_1$ group (methyl) and $C_6$ group (hexyl) end points, but also each of the corresponding individual $C_2$, $C_3$, $C_4$ and $C_5$ groups. In addition, it will be understood that each of the individual points within a stated range of carbon atoms may be further combined to describe subranges that are inherently within the stated overall range. For example, the term "$C_1$–$C_6$-alkyl" includes not only the individual moieties $C_1$ through $C_6$, but also contemplates subranges such as "$C_2$–$C_5$-alkyl."

Based on characterization data, the complex compounds obtained from compounds 1 and 2 are believed to have structure 5:

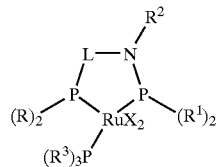

5 wherein R, $R^1$, $R^2$, $R^3$, L and X are defined above. The compounds of the invention which presently are preferred have formula 5 wherein $R^3$ is phenyl, X is chloride, and the substructure $R_2P$—L—$N(R^2)PR^1_2$ collectively represent a group 3 or 4 wherein R is aryl, most preferably phenyl; $R^1$ is aryl, $C_2$–$C_6$ alkyl, or $C_3$–$C_6$ cycloalkyl, preferably phenyl, 3-fluorophenyl, 3,4-difluorophenyl, 4-fluorophenyl, 3,5-difluorophenyl, or 3,4-dichlorophenyl, most preferably 3,4-difluorophenyl; $R^2$ is hydrogen, $C_1$–$C_6$ alkyl, or aryl, most preferably methyl; $R^4$ is hydrogen or $C_1$ to $C_6$ alkyl, most preferably methyl; $R^5$ and $R^6$ are hydrogen; and M is iron, ruthenium, or osmium, most preferably iron, to provide complex 5A or 5B.

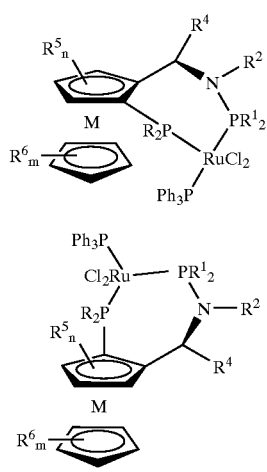

The complex compounds provided by our invention may be prepared by contacting a ruthenium complex of formula having formula 1

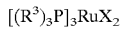     1 with a chiral substantially enantiomerically pure ligand having formula 2

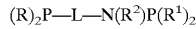     2 in an inert organic solvent, wherein R, $R^1$, $R^2$, $R^3$, L and X are as defined above. The complex compound product may be isolated by standard methods known to those in the art such as crystallization or precipitation. In a preferred embodiment, ruthenium compound 1 is contacted with phosphine-aminophosphine 3 or 4. The amount of ligand 3 or 4 used may be about 1 to 5 moles, preferably about 1 to 1.5 moles, per mole of ruthenium compound 1.

The process is carried out in an inert solvent. Examples of suitable solvents include halocarbon solvents such as dichloromethane, tetrachloroethylene, and chlorobenzene; dipolar aprotic solvents such as acetonitrile, dimethylformamide, and dimethylsulfoxide; cyclic or acyclic ether solvents such as diethyl ether, diisopropyl ether, tert-butyl methyl ether and tetrahydrofuran; ketone solvents such as acetone, methyl ethyl ketone, and diethyl ketone; and aromatic hydrocarbons such as benzene, toluene, or xylene, or mixtures thereof. The preferred solvents are dichloromethane and toluene. The process may be carried out at a temperature between about −50° C. and the boiling point of the solvent, preferably about 20° to 40° C.

Upon completion of the reaction, the ruthenium complex product may be isolated by conventional procedures such as crystallization or distillation. The preferred method of isolation is to precipitate the complex by adding a liquid in which the ruthenium complex is insoluble or substantially insoluble. Examples of such non-solvent liquids include water, $C_3$ to $C_6$ alkanols such as n-propanol, isopropanol, n-butanol, tert-butanol, n-pentanol or n-hexanol, and aliphatic and alicyclic hydrocarbons such as hexane, heptane, and cyclohexane, optionally followed by distillative removal of the solvent from the mixture. The preferred non-solvents are isopropanol and heptane.

The present invention also provides a process for the asymmetric hydrogenation of a 1,3-dicarbonyl compound containing from 5 to 20 carbon atoms to produce the corresponding hydroxycarbonyl compound, which comprises contacting the dicarbonyl compound with hydrogen in the presence of at least one of the ruthenium complex compounds of our invention. The hydrogenation reaction results in the formation of a chiral 3-hydroxycarbonyl compound, which is generally obtained in high enantiomeric excess. The hydrogenation process typically is carried out in the presence of an inert organic solvent. Examples of suitable solvents include lower alcohols such as methanol, ethanol, and isopropanol; aliphatic hydrocarbons such as hexane, heptane, octane and the like; aromatic hydrocarbons such as toluene, xylenes, and the like; cyclic or acyclic ethers such as tert-butyl methyl ether, diisopropyl ether, tetrahydrofuran and the like; halogenated aliphatic or aromatic hydrocarbons such as dichloromethane, tetrachloroethylene, chloroform, chlorobenzene and the like; and polar aprotic solvents such as dimethylformamide, dimethyl sulfoxide and the like. Preferred solvents include methanol or ethanol.

The present invention also provides a process for the asymmetric hydrogenation of an α-hydroxycarbonyl compound containing from 3 to 20 carbon atoms to produce the corresponding 1,2-diol compound, which comprises contacting the hydroxycarbonyl compound with hydrogen in the presence of at least one of the ruthenium complex compounds described above. The hydrogenation reaction results in the formation of a chiral 1,2-diol compound, which is generally obtained in high enantiomeric excess. The hydrogenation process typically is carried out in the presence of an inert organic solvent. Examples of suitable solvents include lower alcohols such as methanol, ethanol, and isopropanol; aliphatic hydrocarbons such as hexane, heptane, octane and the like; aromatic hydrocarbons such as toluene, xylenes, and the like; cyclic or acyclic ethers such as tert-butyl methyl ether, diisopropyl ether, tetrahydrofuran and the like; halogenated aliphatic or aromatic hydrocarbons such as dichloromethane, tetrachloroethylene, chloroform, chlorobenzene and the like; and polar aprotic solvents such as dimethylformamide, dimethyl sulfoxide and the like. Preferred solvents include methanol or ethanol.

The present invention also provides a process for the asymmetric hydrogenation of a β-hydroxycarbonyl compound containing from 4 to 20 carbon atoms to produce the corresponding 1,3-diol compound, which comprises contacting the β-hydroxycarbonyl compound with hydrogen in the presence of at least one of the ruthenium complex compounds described above. The hydrogenation reaction results in the formation of a chiral 1,3-diol compound, which is generally obtained in high enantiomeric excess. The hydrogenation process typically is carried out in the presence of an inert organic solvent. Examples of suitable solvents include lower alcohols such as methanol, ethanol, and isopropanol; aliphatic hydrocarbons such as hexane, heptane, octane and the like; aromatic hydrocarbons such as toluene, xylenes, and the like; cyclic or acyclic ethers such as tert-butyl methyl ether, diisopropyl ether, tetrahydrofuran and the like; halogenated aliphatic or aromatic hydrocarbons such as dichloromethane, tetrachloroethylene, chloroform, chlorobenzene and the like; and polar aprotic solvents such as dimethylformamide, dimethyl sulfoxide and the like. Preferred solvents include methanol or ethanol.

The hydrogenation processes are carried out at elevated pressures by contacting a dicarbonyl or hydroxycarbonyl compound with hydrogen in the presence of a catalytic amount of at least one of the ruthenium complex compounds described above. The amount of ruthenium complex compound used may vary between 0.00005 and 0.5 equivalents based on the reactant compound, with more complex usually providing faster reaction rates. The hydrogen atmosphere may be pure hydrogen or hydrogen mixed with one or more inert gases. The process typically is carried out at hydrogen pressures of 0.07 to 137.9 bars gauge—barg (1–2000 pounds per square inch gauge—psig), preferably between about 3.45 and 69 barg (50–1000 psig). The process normally is operated at a temperature which affords a reasonable rate of conversion, which may be as low as −50° C. but is usually between ambient temperature and the boiling point (or apparent boiling point at elevated pressure) of the lowest boiling component of the reaction mixture.

The ruthenium complex compounds of the present invention also may be used to catalyze other reactions such as asymmetric reductions, asymmetric hydroborations, asymmetric olefin isomerizations, asymmetric hydrosilations, asymmetric allylations, and asymmetric organometallic additions employing a variety of reactants.

EXAMPLES

The novel compounds and processes provided by the present invention are further illustrated by the following examples.

Example 1

Preparation of Dichloro-[(S)-N-diphenylphosphino-N-methyl-1-[(R)-2-(diphenylphosphino)ferrocenyl](ethylamine](triphenylphosphine)ruthenium (5B-a)

(S)—N-Diphenylphosphino-N-methyl-1-[(R)-2-(diphenylphosphino)ferrocenyl] -ethylamine (4a, R=$R^1$=phenyl, $R^2$=$R^4$=methyl, $R^5$=$R^6$=H, M=Fe))(367 mg; 0.60 mmol; 1.2 equiv) was combined with dichlorotris(triphenylphosphine)-ruthenium(II) (479 mg; 0.50 mmol). Dry dichloromethane (10 mL) was added and the flask was evacuated and filled with nitrogen ten times and then stirred overnight at room temperature. Isopropanol (10 mL) was added, resulting in a precipitate. The dichloromethane was removed by distillation in vacuo and the resulting solid was collected by filtration, washed with isopropanol, and dried under vacuum with a nitrogen sweep to afford 0.38 g (73%) of 5B-a.

Example 2

Preparation of Dichloro-[(R)-N-diphenylphosphino-N-methyl-1-[(S)-2-(diphenylphosphino)ferrocenyl]ethylamine](triphenylphosphine)ruthenium(5A-a)

(R)-N-Diphenylphosphino-N-methyl-1-[(S)-2-(diphenylphosphino)ferrocenyl] -ethylamine (3a, R=$R^1$=phenyl, $R^2$=$R^4$=methyl, $R^5$=$R^6$=H, M=Fe))(367 mg; 0.60 mmol; 1.2 equiv) was combined with dichlorotris(triphenylphosphine)-ruthenium(II) (479 mg; 0.50 mmol). Dry dichloromethane (10 mL) was added and the flask was evacuated and filled with nitrogen ten times and then stirred overnight at room temperature. Isopropanol (10 mL) was added, resulting in a precipitate. The dichloromethane was removed by distillation in vacuo and the resulting solid was collected by filtration, washed with isopropanol, and dried under vacuum with a nitrogen sweep to afford 320 mg (61%) of 5A-a.

Example 3

Preparation of Dichloro-[(R)-N-diphenylphosphino-N-methyl-1-[(S)-2-(diphenylphosphino)ferrocenyl]ethylamine](triphenylphosphine)ruthenium (5A-a) in Toluene Dichlorotris(triphenylphosphine)ruthenium(II) (240 mg; 0.25 mmol) was placed in a flask. (R)-N-Diphenylphosphino-N-methyl-1-[(S)-2-(diphenylphosphino)-ferrocenyl]ethylamine (3a, R=$R^1$=phenyl, $R^2$=$R^4$=methyl, $R^5$=$R^6$=H, M= Fe))(168 mg; 0.275 mmol; 1.1 equiv) was dissolved in 5 mL of dry toluene and added. The flask was evacuated and filled with nitrogen ten times and then stirred overnight at room temperature. Heptane (10 mL) was added, resulting in a precipitate, which was collected by filtration, washed with heptane, and dried under vacuum with a nitrogen sweep to afford 77 mg (29%) of 5A-a.

Example 4

Preparation of Dichloro-[(R)-N-diphenylphosphino-1-[(S)-2-(diphenylphosphino)ferrocenyl]ethylamine](triphenylphosphine)ruthenium (5A-b)

(R)-N-Diphenylphosphino-1-[(S)-2-(diphenylphosphino)ferrocenyl]ethylamine (3b, R=$R^1$=phenyl, $R^2$=H, $R^4$=methyl, $R^5$=$R^6$=H, M=Fe))(179 mg; 0.30 mmol; 1.2 equiv) was combined with dichlorotris(triphenylphosphine) ruthenium(II) (240 mg; 0.25 mmol). Dry dichloromethane (5 mL) was added and the flask was evacuated and filled with nitrogen ten times and then stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 185 mg (72%) of 5A-b.

Example 5

Preparation of Dichloro-[(R)-N-diphenylphosphino-N-ethyl-1-[(S)-2-(diphenylphosphino)ferrocenyl]ethylamine](triphenylphosphine)ruthenium(5A-c)

(R)-N-Diphenylphosphino-N-ethyl-1-[(S)-2-(diphenylphosphino)ferrocenyl]-ethylamine (3c, R=$R^1$=phenyl, $R^2$=ethyl, $R^4$=methyl, $R^5$=$R^6$=H, M=Fe))(188 mg; 0.30 mmol; 1.2 equiv) was combined with dichlorotris(triphenylphosphine)-ruthenium(II) (240 mg; 0.25 mmol). Dry dichloromethane (5 mL) was added and the flask was evacuated and filled with nitrogen ten times and then stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 85 mg (32%) of 5A-c.

Example 6

Preparation of Dichloro-[(R)-N-dicyclohexylphosphino-N-methyl-1-[(S)-2-(diphenylphosphino)ferrocenyl]ethylamine](triphenylphosphine)ruthenium (5A-d)

(R)-N-Dicyclohexylphosphino-N-methyl-1-[(S)-2-(diphenylphosphino)-ferrocenyl] ethylamine (3d, R=phenyl, $R^1$=cyclohexyl, $R^2$=$R^4$=methyl, $R^5$=$R^6$=H, M=Fe))(187 mg; 0.30 mmol; 1.2 equiv) was combined with dichlorotris (triphenylphosphine)ruthenium(II) (240 mg; 0.25 mmol). Dry dichloromethane (5 mL) was added and the flask was evacuated and filled with nitrogen ten times and then stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 102 mg (39%) of 5A-d.

Example 7

Preparation of Dichloro-[(R)-N-diethylphosphino-N-methyl-1-[(S)-2-(diphenylphosphino)ferrocenyl]ethylamine](triphenylphosphine)ruthenium (5A-e)

(R)-N-Diethylphosphino-N-methyl-1-[(S)-2-(diphenylphosphino)ferrocenyl]-ethylamine (3e, R=phenyl, $R^1$=ethyl, $R^2$=$R^4$=methyl, $R^5$=$R^6$=H, M=Fe))(100 mg; 0.19 mmol; 1.2 equiv) was combined with dichlorotris (triphenylphosphine)ruthenium(II) (155 mg; 0.16 mmol). Dry dichloromethane (3.5 mL) was added and the flask was evacuated and filled with nitrogen ten times and then stirred overnight at room temperature. Isopropanol (3.5 mL) was added, resulting in a precipitate. The dichloromethane was removed by distillation in vacuo and the resulting solid was collected by filtration, washed with isopropanol, and dried under vacuum with a nitrogen sweep to afford 82 mg (54%) of 5A-e.

Example 8

Preparation of Dichloro-[(R)-N-diphenoxyphosphino-N-methyl-1-[(S)-2-(diphenylphosphino)ferrocenyl]ethylamine](triphenylphosphine)ruthenium (5A-f)

(R)-N-Diphenoxyphosphino-N-methyl-1-[(S)-2-(diphenylphosphino)-ferrocenyl] ethylamine (3f, R=phenyl-Ph, $R^1$=OPh, $R^2$=$R^4$=methyl, $R^5$=$R^6$=H, M=Fe))(386 mg; 0.60 mmol; 1.2 equiv) was combined with dichlorotris (triphenylphosphine)ruthenium(II) (479 mg; 0.50 mmol). Dry dichloromethane (10 mL) was added and the flask was evacuated and filled with nitrogen ten times and then stirred overnight at room temperature. Isopropanol (10 mL) was added, resulting in a precipitate. The dichloromethane was removed by distillation in vacuo and the resulting solid was collected by filtration, washed with isopropanol, and dried under vacuum with a nitrogen sweep to afford 439 mg (81%) of 5A-f.

Example 9

Preparation of Dichloro-[(R)-N-bis(3,5-dimethylphenyl)phosphino-N-methyl-1-[(S)-2-(diphenylphosphino)ferrocenyl]ethylamine](triphenylphosphine)ruthenium(5A-g)

(R)-N-Bis(3,5-dimethylphenyl)phosphino-N-methyl-1-[(S)-2-(diphenylphosphino)ferrocenyl]ethylamine (3g, R=phenyl, $R^1$=3,5-dimethylphenyl, $R^2$=$R^4$= methyl, $R^5$=$R^6$=H, M=Fe))(200 mg; 0.30 mmol; 1.2 equiv) was combined with dichlorotris(triphenylphosphine)ruthenium (II) (240 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 173 mg (63%) of 5A-g.

Example 10

Preparation of Dichloro-[(R)-N-diphenylphosphino-N-isopropyl-1-[(S)-2-(diphenylphosphino)ferrocenyl]ethylamine](triphenylphosphine)ruthenium (5A-h)

(R)—N-Diphenylphosphino-N-isopropyl-1-[(S)-2-(diphenylphosphino)ferrocenyl] ethylamine (3h, R=$R^1$=phenyl, $R^2$=isopropyl, $R^4$=methyl, $R^5$=$R^6$=H, M Fe))(191 mg; 0.30 mmol; 1.2 equiv) was combined with dichlorotris(triphenylphosphine)ruthenium(II) (240 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 177 mg (66%) of 5A-h.

Example 11

Preparation of Dichloro-[(R)-N-bis(4-methoxyphenyl)phosphino-N-methyl-1-[(S)-2-(diphenylphosphino)ferrocenyl]ethylamine](triphenylphosphine)ruthenium (5A-i)

(R)—N-Bis(4-methoxyphenyl)phosphino-N-methyl-1-[(S)-2-(diphenylphosphino)ferrocenyl] ethylamine (3i, R=phenyl, $R^1$=4-methoxyphenyl, $R^2$=$R^4$=methyl, $R^5$=$R^6$=H, M=Fe))(201 mg; 0.30 mmol; 1.2 equiv) was combined with dichlorotris(triphenylphosphine)ruthenium (II) (240 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 196 mg (71%) of 5A-i.

Example 12

Preparation of Dichloro-[(R)-N-bis(3,4-difluorophenyl)phosphino-N-methyl-1-[(S)-2-(diphenylphosphino)ferrocenyl]ethylamine](triphenylphosphine)ruthenium (5A-j)

(R)—N-Bis(3,4-difluorophenyl)phosphino-N-methyl-1-[(S)-2-(diphenylphosphino)ferrocenyl]ethylamine (3j, R=phenyl, $R^1$=3,4-difluorophenyl, $R^2$=$R^4$= methyl, $R^5$=$R^6$=H, M=Fe))(222 mg; 0.325 mmol; 1.3 equiv) was combined with dichlorotris(triphenylphosphine)ruthenium (II) (240 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 198 mg (71%) of 5A-j. Anal. Calcd. for $C_{55}H_{46}Cl_2F_4FeNP_3Ru$: C, 59.10; H, 4.15; N, 1.25; Found, 59.82; H, 4.28; N, 1.12.

Example 13

Preparation of Dichloro-[(R)-N-bis(3,4-dichlorophenyl)phosphino-N-methyl-1-[(S)-2-(diphenylphosphino)ferrocenyl]ethylamine](triphenylphosphine)ruthenium (5A-k)

(R)—N-Bis(3,4-dichlorophenyl)phosphino-N-methyl-1-[(S)-2-(diphenylphosphino)ferrocenyl] ethylamine (3k, R=phenyl, $R^1$=3,4-dichlorophenyl, $R^2$=$R^4$= methyl, $R^5$=$R^6$=H, M=Fe))(305 mg; 0.407 mmol; 1.3 equiv) was combined with dichlorotris(triphenylphosphine)ruthenium (II) (300 mg; 0.313 mmol). The flask was evacuated and filled with nitrogen ten times and dry dichloromethane (6 mL) was added. The reaction mixture was stirred overnight at room temperature. Isopropanol (6 mL) was added, resulting in a precipitate. The dichloromethane was removed by distillation in vacuo and the resulting solid was collected by filtration, washed with isopropanol, and dried under vacuum with a nitrogen sweep to afford 303 mg (82%) of 5A-k.

Example 14

Preparation of Dichloro-[(R)-N-bis(3,5-difluorophenyl)phosphino-N-methyl-1-[(S)-2-(diphenylphosphino)ferrocenyl]ethylamine](triphenylphosphine)ruthenium (5A-l)

(R)—N-Bis(3,5-difluorophenyl)phosphino-N-methyl-1-[(S)-2-(diphenylphosphino)ferrocenyl]ethylamine (3l, R=phenyl, $R^1$=3,5-difluorophenyl, $R^2$=$R^4$= methyl, $R^5$=$R^6$=H, M=Fe))(222 mg; 0.325 mmol; 1.3 equiv) was combined with dichlorotris(triphenylphosphine)ruthenium (II) (250 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 193 mg (69%) of 5A-l.

Example 15

Preparation of Dichloro-[(R)-N-bis(3,5-dichlorophenyl)phosphino-N-methyl-1-[(S)-2-(diphenylphosphino)ferrocenyl]ethylamine](triphenylphosphine)ruthenium (5A-m)

(R)—N-Bis(3,5-dichlorophenyl)phosphino-N-methyl-1-[(S)-2-(diphenylphosphino)ferrocenyl] ethylamine (3m, R=phenyl, $R^1$=3,5-dichlorophenyl, $R^2$=$R^4$= methyl, $R^5$=$R^6$=H, M=Fe))(247 mg; 0.325 mmol; 1.3 equiv) was combined with dichlorotris(triphenylphosphine)ruthenium (II) (240 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 238 mg (80%) of 5A-m.

Example 16

Preparation of Dichloro-[(R)-N-bis(4-fluorophenyl)phosphino-N-methyl-1-[(S)-2-(diphenylphosphino)ferrocenyl]ethylamine](triphenylphosphine)ruthenium (5A-n)

(R)—N-Bis(4-fluorophenyl)phosphino-N-methyl-1-[(S)-2-(diphenylphosphino)ferrocenyl] ethylamine (3n, R=phenyl, $R^1$=4-fluorophenyl, $R^2$=$R^4$=methyl, $R^5$=$R^6$=H, M=Fe))(210 mg; 0.325 mmol; 1.3 equiv) was combined with dichlorotris(triphenylphosphine)ruthenium (II) (250 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 0.22 g (81%) of 5A-n.

Example 17

Preparation of Dichloro-[(R)-N-bis(3-fluorophenyl)phosphino-N-methyl-1-[(S)-2-(diphenylphosphino)ferrocenyl]ethylamine](triphenylphosphine)ruthenium (5A-o)

(R)—N-Bis(3-fluorophenyl)phosphino-N-methyl-1-[(S)-2-(diphenylphosphino)-ferrocenyl] ethylamine (3o, R=phenyl, $R^1$=3-fluorophenyl, $R^2$=$R^4$=methyl, $R^5$=$R^6$H, M=Fe))(210 mg; 0.325 mmol; 1.3 equiv) was combined with dichlorotris(triphenylphosphine)ruthenium(II) (250 mg; 0.25 mmol). The flask was evacuated and filled with nitrogen ten times and dry dichloromethane (5 mL) was added. The reaction mixture was stirred overnight at room temperature. Isopropanol (5 mL) was added, resulting in a precipitate. The dichloromethane was removed by distillation in vacuo and the resulting solid was collected by filtration, washed with isopropanol, and dried under vacuum with a nitrogen sweep to afford 207 mg (77%) of 5A-o.

Example 18

Hydrogenation of Methyl Acetoacetate to Methyl (S)-3-hydroxybutyrate using Complex 5B-a

Complex 5B-a from Example 1 (2.6 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times. Assay of the product solution by chiral GC showed 100% conversion to methyl (S)-3-hydroxybutyrate with 90.7% ee. Chiral GC [30 m×0.25 mm Cyclosil-B (J&W Scientific), 0.25 µm film thickness, 100° C. isothermal]: $t_R$=6.29 min (methyl acetoacetate), $t_R$=6.54 min [methyl (S)-3-hydroxybutyrate], $t_R$=6.71 min [methyl (R)-3-hydroxybutyrate].

Example 19

Hydrogenation of Ethyl Acetoacetate to Ethyl (S)-3-hydroxybutyrate Using Complex 5B-a

Complex 5B-a from Example 1 (2.6 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 89% conversion to ethyl (S)-3-hydroxybutyrate with 89.4% ee. Chiral GC [30 m×0.25 mm Cyclosil-B (J&W Scientific), 0.25 µm film thickness, 100° C. isothermal]: $t_R$=8.36 min (ethyl acetoacetate), $t_R$=8.69 min [ethyl (S)-3-hydroxybutyrate], $t_R$=8.93 min [ethyl (R)-3-hydroxybutyrate].

Example 20

Hydrogenation of Ethyl Acetoacetate to Ethyl (S)-3-hydroxybutyrate Using Complex 5B-a at 100 psig Hydrogen

Complex 5B-a from Example 1 (2.6 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 6.9 barg (100 psig) with hydrogen and stirred at ambient temperature for 6 hours. The vessel was vented, then pressurized with argon and vented five times, and the solution was assayed by chiral GC to indicate 100% conversion to ethyl (S)-3-hydroxybutyrate with 88.6% ee.

Example 21

Hydrogenation of Methyl Propionylacetate to Methyl (S)-3-hydroxypentanoate Using Complex 5B-a

Complex 5B-a from Example 1 (2.6 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (S)-3-hydroxypentanoate with 86.2% ee. Chiral GC [30 m×0.25 mm Cyclosil-B (J&W Scientific), 0.25 µm film thickness, 70° C. isothermal]: $t_R$= 9.72 min (methyl propionylacetate), $t_R$=10.34 min [methyl (S)-3-hydroxypentanoate], $t_R$=10.80 min [methyl (R)-3-hydroxypentanoate].

Example 22

Hydrogenation of Methyl Acetoacetate to Methyl (R)-3-hydroxybutyrate Using Complex 5A-a

Complex 5A-a from Example 2 (2.6 mg; 0.0025 mmol; 0.005 equiv) was placed in a reaction vessel, which was pressurized with argon and vented five times. Argon-degassed methanol (2 mL) was added and the mixture was stirred for 15 minites. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 89.5% ee.

Example 23

Hydrogenation of Ethyl Acetoacetate to Ethyl (R)-3-hydroxybutyrate Using Complex 5A-a

Complex 5A-a from Example 2 (2.6 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 86.2% conversion to ethyl (R)-3-hydroxybutyrate with 87.6% ee.

Example 24

Hydrogenation of Methyl Propionylacetate to Methyl (R)-3-hydroxypentanoate Using Complex 5A-a Complex 5A-a from Example 2 (2.6 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxypentanoate with 89.4% ee.

Example 25

Hydrogenation of Methyl Acetoacetate to Methyl (R)-3-hydroxybutyrate Using Complex 5A-a Complex 5A-a from Example 3 (2.6 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 87.4% ee.

Example 26

Hydrogenation of Methyl Acetoacetate to Methyl (R)-3-hydroxybutyrate Using Complex 5A-c Complex 5A-c from Example 5 (2.6 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 76.2% ee.

Example 27

Hydrogenation of Ethyl Acetoacetate to Ethyl (R)-3-hydroxybutyrate Using Complex 5A-c Complex 5A-c from Example 5 (2.6 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 84.8% conversion to ethyl (R)-3-hydroxybutyrate with 71.6% ee.

Example 28

Hydrogenation of Methyl Acetoacetate to Methyl (R)-3-hydroxybutyrate Using Complex 5A-g Complex 5A-g from Example 9 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 82.5% ee.

Example 29

Hydrogenation of Ethyl Acetoacetate to Ethyl (R)-3-hydroxybutyrate Using Complex 5A-g Complex 5A-g from Example 9 (2.8 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to ethyl (R)-3-hydroxybutyrate with 81.7% ee.

Example 30

Hydrogenation of Methyl Propionylacetate to Methyl (R)-3-hydroxypentanoate Using Complex 5A-g Complex 5A-g from Example 9 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxypentanoate with 79.3% ee.

Example 31

Hydrogenation of Methyl Acetoacetate to Methyl (R)-3-hydroxybutyrate Using Complex 5A-i Complex 5A-i from Example 11 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 97.1% conversion to methyl (R)-3-hydroxybutyrate with 85.4% ee.

Example 32

Hydrogenation of Ethyl Acetoacetate to Ethyl (R)-3-hydroxybutyrate Using Complex 5A-i Complex 5A-i from Example 11 (2.8 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 33.5% conversion to ethyl (R)-3-hydroxybutyrate with 92.7% ee.

Example 33

Hydrogenation of Methyl Propionylacetate to Methyl (R)-3-hydroxypentanoate Using Complex 5A-i Complex 5A-i from Example 11 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 24.3% conversion to methyl (R)-3-hydroxypentanoate with 84.9% ee.

Example 34

Hydrogenation of Methyl Acetoacetate to Methyl (R)-3-hydroxybutyrate Using Complex 5A-j in Methanol Complex 5A-j from Example 12 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl acetoacetate (54 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 99.3% conversion to methyl (R)-3-hydroxybutyrate with 93.9% ee.

Example 35

Hydrogenation of Methyl Acetoacetate to Methyl (R)-3-hydroxybutyrate Using Complex 5A-j in Ethanol Complex 5A-j from Example 12 (2.8 mg; 0.0025 mmol; 0.005 equiv) and methyl acetoacetate (54 µL; 0.5 mmol) were placed in a reaction vessel, which was pressurized with argon and vented five times. Argon-degassed ethanol (5 mL) was added and the reaction mixture was pressurized with argon and vented five times and then pressurized to 20.7 barg (300 psig) with hydrogen and stirred at ambient temperature for 12 hours. The vessel was vented, then pressurized with argon and vented five times, and the solution was assayed by chiral GC to indicate 100% conversion to methyl (R)-3-hydroxybutyrate with 96.0% ee.

Example 36

Hydrogenation of Ethyl Acetoacetate to Ethyl (R)-3-hydroxybutyrate Using Complex 5A-j Complex 5A-j from Example 12 (2.8 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to ethyl (R)-3-hydroxybutyrate with 95.4% ee.

Example 37

Hydrogenation of Methyl Propionylacetate to Methyl (R)-3-hydroxypentanoate Using Complex 5A-j Complex 5A-j from Example 12 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 μL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 98.6% conversion to methyl (R)-3-hydroxypentanoate with 95.6% ee.

Example 38

Hydrogenation of Ethyl Benzoylacetate to Ethyl (S)-3-hydroxy-3-phenylpropionate Using Complex 5A-j Complex 5A-j from Example 12 (2.8 mg; 0.0025 mmol; 0.005 equiv) and ethyl benzoylacetate (86 μL; 0.5 mmol) were placed in a reaction vessel, which was pressurized with argon and vented five times. Argon-degassed ethanol (5 mL) was added and the mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by $^1$H NMR to indicate 99% conversion to ethyl (S)-3-hydroxy-3-phenylpropionate with 94.9% ee by chiral HPLC. $^1$H NMR (CDCl$_3$) δ 7.4–7.2 (5H, m); 5.130 (1H, dd, J=4.36, 8.48 Hz); 4.178 (2H, q, J=7.17 Hz); 3.2 (1H, br s); 2.764 (1H, dd, J=8.58, 16.30 Hz); 2.691 (1H, dd, J=4.33, 16.33 Hz); 1.259 (3H, t, J=7.17 Hz). Chiral HPLC (250×4.6 mm Chiralpak AD-H [Chiral Technologies], 95:5 hexane:isopropanol, 1 mL/min, λ=254 nm): $t_R$(ethyl benzoylacetate) 12.2 min, $t_R$ 17.9 min [ethyl (R)-3-hydroxy-3-phenylpropionate], $t_R$ 19.2 min [ethyl (S)-3-hydroxy-3-phenylpropionate].

Example 39

Hydrogenation of Dimethyl 3-Oxooctanedioate to Dimethyl (R)-3-hydroxyoctanedioate Using Complex 5A-j in Ethanol Complex 5A-j from Example 12 (5.6 mg; 0.005 mmol; 0.005 equiv) and dimethyl 3-oxooctanedioate (216 mg; 1.0 mmol) were placed in a reaction vessel, which was pressurized with argon and vented five times. Argon-degassed ethanol (5 mL) was added and the reaction mixture was pressurized with argon and vented five times and then pressurized to 20.7 barg (300 psig) with hydrogen and stirred at ambient temperature for 12 hours. The vessel was vented, then pressurized with argon and vented five times and the solvent was stripped. Assay of the product by $^1$H NMR showed >99% conversion to dimethyl (R)-3-hydroxyoctanedioate with 97.7% ee according to chiral GC analysis. $^1$H NMR (CDCl$_3$) δ 4.04–3.98 (1H, m); 3.716 (s, 3H); 3.669 (s, 3H); 2.55–2.43 (m, 2H); 2.37–2.31 (m, 2H); 1.76–1.35 (m, 6H).Chiral GC [30 m×0.25 mm Cyclosil-B (J&W Scientific), 0.25 μm film thickness, 155° C. isothermal]: $t_R$=25.25 min [dimethyl (S)-3-hydroxyoctanedioate], $t_R$=25.80 min [dimethyl (R)-3-hydroxyoctanedioate].

Example 40

Hydrogenation of Dimethyl 3-Oxooctanedioate to Dimethyl (R)-3-hydroxyoctanedioate Using Complex 5A-j in n-Butanol Complex 5A-j from Example 12 (5.6 mg; 0.005 mmol; 0.005 equiv) and dimethyl 3-oxooctanedioate (216 mg; 1.0 mmol) were placed in a reaction vessel, which was pressurized with argon and vented five times. Argon-degassed n-butanol (5 mL) was added and the reaction mixture was pressurized with argon and vented five times and then pressurized to 20.7 barg (300 psig) with hydrogen and stirred at ambient temperature for 12 hours. The vessel was vented, then pressurized with argon and vented five times and the solvent was stripped. Assay of the product by $^1$H NMR showed 68% conversion to dimethyl (R)-3-hydroxyoctanedioate with 98.0% ee according to chiral GC analysis.

Example 41

Hydrogenation of 1-Hydroxy-2-butanone to (R)-1,2-Butanediol using Complex 5A-j in Methanol Complex 5A-j from Example 12 (2.8 mg; 0.0025 mmol; 0.005 equiv) and 1hydroxy-2-butanone (45 μL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times. Analysis of the reaction mixture by chiral GC indicated 81.9% conversion to 1,2-butanediol. The solvent was stripped and the residue was converted to the diacetate using acetic anhydride (0.14 mL; 1.5 mmol; 3 equiv) and triethylamine (0.28 mL; 2.0 mmol; 4 equiv) with a catalytic amount of DMAP in 2.5 mL of dichloromethane. Assay of the 1,2-diacetoxybutane thus produced indicated 87.4% ee of the (R)-enantiomer according to chiral GC analysis. Chiral GC [30 m×0.25 mm Cyclosil-B (J&W Scientific), 0.25 μm film thickness, 100° C. isothermal]: $t_R$= 7.23 min (1-hydroxy-2-butanone), $t_R$=13.8, 14.1 min (1,2-butanediol), $t_R$ 16.85 min [(S)-1,2-diacetoxybutane], $t_R$=17.75 min [(R)-1,2-diacetoxybutane].

Example 42

Hydrogenation of 1-Hydroxy-2-butanone to (R)-1,2-Butanediol Using Complex 5A-j in Ethanol Complex 5A-j from Example 12 (2.8 mg; 0.0025 mmol; 0.005 equiv) and 1hydroxy-2-butanone (45 μL; 0.5 mmol) were placed in a reaction vessel, which was pressurized with argon and vented five times. Argon-degassed ethanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times. Analysis of the reaction mixture by chiral GC indicated 93.4% conversion to 1,2-butanediol. The solvent was stripped and the residue was converted to the diacetate using acetic anhydride (0.14 mL; 1.5 mmol; 3 equiv) and triethylamine (0.28 mL; 2.0 mmol; 4 equiv) with a catalytic amount of DMAP in 2.5 mL of dichloromethane. Assay of the 1,2-diacetoxybutane thus produced indicated 88.8% ee of the (R)-enantiomer according to chiral GC analysis.

Example 43

Hydrogenation of 1-Hydroxy-3-butanone to (R)-1,3-Butanediol Using Complex 5A-j

Complex 5A-j from Example 12 (2.8 mg; 0.0025 mmol; 0.005 equiv) and 1-hydroxy-3-butanone (45 μL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times. Analysis of the reaction mixture by chiral GC indicated 99.2% conversion to 1,3-butanediol. The solvent was stripped and the residue was converted to the diacetate using acetic anhydride (0.14 mL; 1.5 mmol; 3 equiv) and triethylamine (0.28 mL; 2.0 mmol; 4 equiv) with a catalytic amount of DMAP in 2.5 mL of dichloromethane. Assay of the 1,3-diacetoxybutane thus produced indicated 81.8% ee of the (R)-enantiomer according to chiral GC analysis. Chiral GC [30 m×0.25 mm Cyclosil-B (J&W Scientific), 0.25 μm film thickness, 100° C. isothermal]: $t_R$= 8.82 min (1-hydroxy-3-butanone), $t_R$=16.09 min (1,3-butanediol), $t_R$ 20.65 min [(S)-1,3-diacetoxybutane], $t_R$=23.20 min [(R)-1,3-diacetoxybutane].

Example 44

Hydrogenation of 2-Hydroxyacetophenone to (R)-1-Phenyl-1,2-ethanediol using Complex 5A-j

Complex 5A-j from Example 12 (2.8 mg; 0.0025 mmol; 0.005 equiv) and 2hydroxy-acetophenone (68 mg; 0.5 mmol) were placed in a reaction vessel, which was pressurized with argon and vented five times. Argon-degassed ethanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times. Analysis of the reaction mixture by chiral GC indicated 11.2% conversion to (R)-1-phenyl-1,2-ethanediol with 77.6% ee according to chiral GC. Chiral GC [30 m×0.25 mm Cyclosil-B (J&W Scientific), 0.25 μm film thickness, 150° C. isothermal]: $t_R$=12.94 min (2-hydroxy-acetophenone), $t_R$ 28.30 min [(S)-1-phenyl-1,2-ethanediol], $t_R$=29.21 min [(R)-1-phenyl-1,2-ethanediol].

Example 45

Hydrogenation of Methyl Acetoacetate to Methyl (R)-3-hydroxybutyrate Using Complex 5A-k

Complex 5A-k from Example 13 (3.0 mg; 0.0025 mmol; 0.005 equiv) and methyl acetoacetate (54 μL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 87.9% ee.

Example 46

Hydrogenation of Ethyl Acetoacetate to Ethyl (R)-3-hydroxybutyrate Using Complex 5A-k

Complex 5A-k from Example 13 (3.0 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 μL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 59.2% conversion to ethyl (R)-3-hydroxybutyrate with 94.0% ee.

Example 47

Hydrogenation of Methyl Propionylacetate to Methyl (R)-3-hydroxypentanoate Using Complex 5A-k

Complex 5A-k from Example 13 (3.0 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 μL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxypentanoate with 89.7% ee.

Example 48

Hydrogenation of Ethyl Benzoylacetate to Ethyl (S)-3-hydroxy-3-phenylpropionate Using Complex 5A-k

Complex 5A-k from Example 13 (3.0 mg; 0.0025 mmol; 0.005 equiv) and ethyl benzoylacetate (86 μL; 0.5 mmol) were placed in a reaction vessel, which was pressurized with argon and vented five times. Argon-degassed ethanol (5 mL) was added and the mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by $^1$H NMR to indicate 87% conversion to ethyl (S)-3-hydroxy-3-phenylpropionate with 91.3% ee by chiral HPLC.

Example 49

Hydrogenation of Dimethyl 3-Oxooctanedioate to Dimethyl (R)-3-hydroxyoctanedioate Using Complex 5A-k

Complex 5A-k from Example 13 (5.9 mg; 0.005 mmol; 0.005 equiv) and dimethyl 3-oxooctanedioate (216 mg; 1.0 mmol) were placed in a reaction vessel, which was pressurized with argon and vented five times. Argon-degassed ethanol (5 mL) was added and the reaction mixture was pressurized with argon and vented five times and then pressurized to 20.7 barg (300 psig) with hydrogen and stirred at ambient temperature for 12 hours. The vessel was vented, then pressurized with argon and vented five times and the solvent was stripped. Assay of the product by $^1$H NMR showed >99% conversion to dimethyl (R)-3-hydroxy-octanedioate with 97.5% ee according to chiral GC analysis.

Example 50

Hydrogenation of 1-Hydroxy-2-butanone to (R)-1,2-Butanediol Using Complex 5A-k

Complex 5A-k from Example 13 (3.0 mg; 0.0025 mmol; 0.005 equiv) and 1hydroxy-2-butanone (45 µL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times. Analysis of the reaction mixture by chiral GC indicated 65.6% conversion to 1,2-butanediol. The solvent was stripped and the residue was converted to the diacetate using acetic anhydride (0.14 mL; 1.5 mmol; 3 equiv) and triethylamine (0.28 mL; 2.0 mmol; 4 equiv) with a catalytic amount of DMAP in 2.5 mL of dichloromethane. Assay of the 1,2-diacetoxybutane thus produced indicated 84.6% ee of the (R)-enantiomer according to chiral GC analysis.

Example 51

Hydrogenation of Methyl Acetoacetate to Methyl (R)-3-hydroxybutyrate Using Complex 5A-l Complex 5A-l from Example 14 (2.8 mg; 0.0025 mmol; 0.005 equiv) and methyl acetoacetate (54 µL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 84.4% ee.

Example 52

Hydrogenation of Ethyl Acetoacetate to Ethyl (R)-3-hydroxybutyrate Using Complex 5A-l Complex 5A-l from Example 14 (2.8 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to ethyl (R)-3-hydroxybutyrate with 92.5% ee.

Example 53

Hydrogenation of Methyl Propionylacetate to Methyl (R)-3-hydroxypentanoate Using Complex 5A-l Complex 5A-l from Example 14 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 µL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxypentanoate with 86.1% ee.

Example 54

Hydrogenation of Methyl Acetoacetate to Methyl (R)-3-hydroxybutyrate Using Complex 5A-n Complex 5A-n from Example 16 (2.7 mg; 0.0025 mmol; 0.005 equiv) and methyl acetoacetate (54 µL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxybutyrate with 89.6% ee.

Example 55

Hydrogenation of Ethyl Acetoacetate to Ethyl (R)-3-hydroxybutyrate Using Complex 5A-n Complex 5A-n from Example 16 (2.7 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 µL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to ethyl (R)-3-hydroxybutyrate with 91.6% ee.

Example 56

Hydrogenation of Methyl Propionylacetate to Methyl (R)-3-hydroxypentanoate Using Complex 5A-n Complex 5A-n from Example 16 (2.8 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 μL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 98.8% conversion to methyl (R)-3-hydroxypentanoate with 91.9% ee.

Example 57

Hydrogenation of Methyl Acetoacetate to Methyl (R)-3-hydroxybutyrate Using Complex 5A-o Complex 5A-o from Example 17 (2.7 mg; 0.0025 mmol; 0.005 equiv) and methyl acetoacetate (54 μL; 0.5 mmol) were placed in a reaction vessel, which was pressurized with argon and vented five times. Argon-degassed methanol (5 mL) was added and the reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 99.8% conversion to methyl (R)-3-hydroxybutyrate with 92.9% ee.

Example 58

Hydrogenation of Ethyl Acetoacetate to Ethyl (R)-3-hydroxybutyrate Using Complex 5A-o Complex 5A-o from Example 17 (2.7 mg; 0.0025 mmol; 0.005 equiv) was placed in a reaction vessel, which was pressurized with argon and vented five times. Argon-degassed ethanol (2 mL) was added and the mixture was stirred for 15 minutes. Ethyl acetoacetate (64 μL; 0.5 mmol) dissolved in 2 mL of argon-degassed ethanol was added and was washed in with 1.0 mL of argon-degassed ethanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 99.8% conversion to ethyl (R)-3-hydroxybutyrate with 92.7% ee.

Example 59

Hydrogenation of Methyl Propionylacetate to Methyl (R)-3-hydroxypentanoate Using Complex 5A-o Complex 5A-o from Example 17 (2.7 mg; 0.0025 mmol; 0.005 equiv) was placed in a reaction vessel, which was pressurized with argon and vented five times. Argon-degassed methanol (2 mL) was added and the mixture was stirred for 15 minutes. Methyl propionylacetate (63 μL; 0.5 mmol) dissolved in 2 mL of argon-degassed methanol was added and was washed in with 1.0 mL of argon-degassed methanol. The reaction mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by chiral GC to indicate 100% conversion to methyl (R)-3-hydroxypentanoate with 94.3% ee.

Example 60

Hydrogenation of Ethyl Benzoylacetate to Ethyl (S)-3-hydroxy-3-phenylpropionate Using Complex 5A-o Complex 5A-o from Example 17 (2.7 mg; 0.0025 mmol; 0.005 equiv) and ethyl benzoylacetate (86 μL; 0.5 mmol) were placed in a reaction vessel, which was pressurized with argon and vented five times. Argon-degassed ethanol (5 mL) was added and the mixture was pressurized with argon and vented five times and then pressurized to 20.7 barg (300 psig) with hydrogen and stirred at ambient temperature for 6 hours. The vessel was vented, then pressurized with argon and vented five times, and the solution was assayed by $^1$H NMR to indicate 99% conversion to ethyl (S)-3-hydroxy-3-phenylpropionate with 80.2% ee by chiral HPLC.

The invention has been described in detail with particular reference to preferred embodiments thereof, but it will be understood that variations and modifications can be effected within the spirit and scope of the invention.

I claim:

1. A ruthenium complex compound comprising a ruthenium compound having formula 1:

$$[(R^3)_3P]_3RuX_2 \qquad 1$$

and a chiral substantially enantiomerically pure ligand having formula 2:

$$(R)_2P{-}L{-}N(R^2)P(R^1)_2 \qquad 2$$

wherein

R, $R^2$, and $R^3$ are, independently, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

$R^1$ is substituted or unsubstituted, branched- or straight-chain $C_1$–$C_{20}$ alkyl, substituted or unsubstituted, branched- or straight-chain $C_1$–$C_{20}$ alkoxy, substituted or unsubstituted $C_3$–$C_8$ cycloalkyl, substituted or unsubstituted $C_3$–$C_8$ cycloalkoxy, substituted or unsubstituted $C_6$–$C_{20}$ carbocyclic aryl, substituted or unsubstituted $C_6$–$C_{20}$ carbocyclic aryloxy;

X is fluoride, chloride, bromide, or iodide; and

L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenylmethylene wherein L is substantially enantiomerically pure.

2. A complex compound according to claim 1 wherein X is chloride, $R^3$ is phenyl and $(R)_2P$—L—$N(R^2)P(R^1)_2$ represents structure 3 or 4:

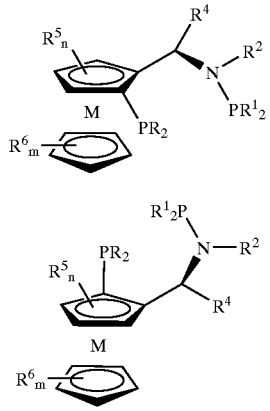

wherein
$R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;
n is 0 to 3;
m is 0 to 5; and
M is a metal of Group IVB, VB, VIIB, VIIB or VIII.

3. A complex compound according to claim 2 wherein R is aryl; $R^1$ is aryl, aryloxy, $C_2$–$C_6$ alkyl, or $C_3$–$C_6$ cycloalkyl; $R^2$ is hydrogen, $C_1$–$C_6$ alkyl, or aryl; $R^4$ is hydrogen or $C_1$ to $C_6$ alkyl; $R^5$ and $R^6$ are hydrogen; and M is iron, ruthenium, or osmium.

4. A complex compound according to claim 2 wherein R is phenyl; $R^1$ is phenyl, 3-fluorophenyl, 3,4-difluorophenyl, 4-fluorophenyl, 3,5-difluorophenyl, or 3,4-dichlorophenyl; $R^2$ is hydrogen, methyl, ethyl, or isopropyl; $R^4$ is hydrogen or $C_1$ to $C_6$ alkyl; $R^5$ and $R^6$ are hydrogen; and M is iron.

5. A compound having formula 5:

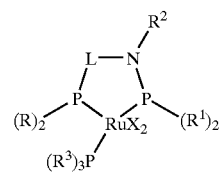

wherein
R, $R^2$, and $R^3$ are, independently, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;
$R^1$ is substituted or unsubstituted, branched- or straight-chain $C_1$–$C_{20}$ alkyl, substituted or unsubstituted, branched- or straight-chain $C_1$–$C_{20}$ alkoxy, substituted or unsubstituted $C_3$–$C_8$ cycloalkyl, substituted or unsubstituted $C_3$–$C_8$ cycloalkoxy, substituted or unsubstituted $C_6$–$C_{20}$ carbocyclic aryl, or substituted or unsubstituted $C_6$–$C_{20}$ carbocyclic aryloxy;
X is fluoride, chloride, bromide, or iodide; and
L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenymethylene wherein L is substantially enantiomerically pure.

6. A compound according to claim 5 wherein X is chloride, $R^3$ is phenyl and $(R)_2P$—L—$N(R^2)P(R^1)_2$ represent structures 3 or 4

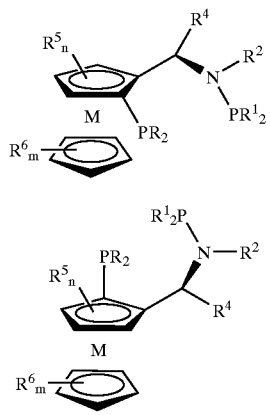

wherein $R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, or oxygen;
n is 0 to 3;
m is 0 to 5; and
M is a metal of Groups IVB, VB, VIIB, VIIB or VIII.

7. A complex compound according to claim 6 wherein R is aryl; $R^1$ is aryl, aryloxy, $C_2$–$C_6$ alkyl, or $C_3$–$C_6$ cycloalkyl; $R^2$ is hydrogen, $C_1$–$C_6$ alkyl, or aryl; $R^4$ is hydrogen or $C_1$ to $C_6$ alkyl; $R^5$ and $R^6$ are hydrogen; and M is iron, ruthenium, or osmium.

8. A compound according to claim 6 wherein R is phenyl; $R^1$ is phenyl, 3-fluorophenyl, 3,4-difluorophenyl, 4-fluorophenyl, 3,5-difluorophenyl, or 3,4-dichlorophenyl;
$R^2$ is hydrogen, methyl, ethyl, or isopropyl; $R^4$ is hydrogen or $C_1$ to $C_6$ alkyl; $R^5$ and $R^6$ are hydrogen; and M is iron.

9. A process for the preparation of a ruthenium complex compound defined in claim 1 which comprises contacting a ruthenium compound having formula 1

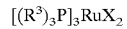

with a chiral substantially enantiomerically pure, ligand having formula 2

in an inert solvent.

10. A process for the preparation of a compound defined in claim 5 which comprises contacting a ruthenium complex having formula 1:

$$[(R^3)_3P]_3RuX_2 \quad 1$$

with a chiral, substantially enantiomerically pure, ligand having formula 3 or 4

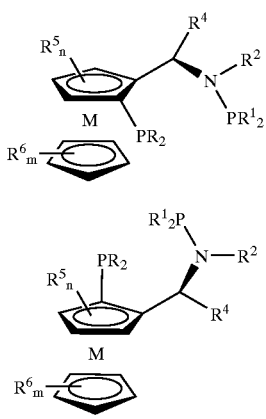

in an inert solvent selected from halocarbon solvents, dipolar aprotic solvents, cyclic or acyclic ether solvents, ketone solvents or aromatic hydrocarbons at a temperature of between about −50° C. and the boiling point of the solvent; wherein R and $R^2$ are, independently, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, or oxygen;

$R^1$ is substituted or unsubstituted, branched- or straight-chain $C_1$–$C_{20}$ alkyl, substituted or unsubstituted, branched- or straight-chain $C_1$–$C_{20}$ alkoxy, substituted or unsubstituted $C_3$–$C_8$ cycloalkyl, substituted or unsubstituted $C_3$–$C_8$ cycloalkoxy, substituted or unsubstituted $C_6$–$C_{20}$ carbocyclic aryl, substituted or unsubstituted $C_6$–$C_{20}$ carbocyclic aryloxy;

$R^3$ is phenyl;

$R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, or oxygen;

n is 0 to 3;

m is 0 to 5; and

M is a metal of Groups IVB, VB, VIIB, VIIB or VIII.

11. Process according to claim 10 wherein the inert solvent is dichloromethane, tetrachloroethylene, chlorobenzene, acetonitrile, dimethylformamide, dimethylsulfoxide, diethyl ether, diisopropyl ether, tert-butyl methyl ether, tetrahydrofuran, acetone, methyl ethyl ketone, diethyl ketone, benzene, toluene, xylene, or a mixture of any two or more thereof; R is aryl; $R^1$ is aryl, aryloxy, $C_2$–$C_6$ alkyl, or $C_3$–$C_6$ cycloalkyl; $R^2$ is hydrogen, $C_1$–$C_6$ alkyl, or aryl; $R^4$ is hydrogen or $C_1$ to $C_6$ alkyl; $R^5$ and $R^6$ are hydrogen; X is chloride; M is iron, ruthenium, or osmium; and the process is carried out at a temperature of about 20° to 40° C.

12. Process according to claim 10 wherein the inert solvent is selected from dichloromethane or toluene; R is phenyl; $R^1$ is phenyl, 3-fluorophenyl, 3,4difluorophenyl, 4-fluorophenyl, 3,5-difluorophenyl, or 3,4-dichlorophenyl; R2 is hydrogen, methyl, or ethyl; $R^4$ is hydrogen or $C_1$ to $C_6$ alkyl; $R^5$ and $R^6$ are hydrogen; M is iron; and the process is carried out at a temperature of about 20 to 40° C.

13. Process for the asymmetric hydrogenation of a 1,3-dicarbonyl compound to produce the corresponding hydroxycarbonyl compound which comprises contacting the dicarbonyl compound with hydrogen in the presence of a solution of a ruthenium complex compound defined in claim 1 in an inert organic colvent.

14. Process for the asymmetric hydrogenation of a 1,3-dicarbonyl compound containing from 5 to 20 carbon atoms to produce the corresponding hydroxycarbonyl compound which comprises contacting the dicarbonyl compound with hydrogen in the presence of a solution of a ruthenium complex compound defined in claim 2 in an inert organic solvent to form a reaction mixture, wherein the amount of ruthenium complex compound is about 0.00005 to 0.5 equivalents based on the 1,3-dicarbonyl reactant compound; and the process is carried out at hydrogen pressures of 0.07 to 137.9 bars gauge and at a temperature between ambient temperature and the boiling point of the lowest boiling component of the reaction mixture.

15. Process according to claim 14 wherein the hydrogen pressure is between about 3.45 and 69 barg.

16. Process for the asymmetric hydrogenation of an α-hydroxycarbonyl compound to produce the corresponding 1,2-diol compound which comprises contacting the hydroxycarbonyl compound with hydrogen in the presence of a solution of a ruthenium complex compound defined in claim 1 in an inert organic colvent.

17. Process for the asymmetric hydrogenation of an α-hydroxycarbonyl compound containing from 3to 20 carbon atoms to produce the corresponding 1,2-diol compound which comprises contacting the hydroxycarbonyl compound with hydrogen in the presence of a solution of a ruthenium complex compound defined in claim 2 in an inert organic solvent to form a reaction mixture, wherein the amount of ruthenium complex compound is about 0.00005 to 0.5 equivalents based on the α-hydroxycarbonyl reactant compound; and the process is carried out at hydrogen pressures of 0.07 to 137.9 bars gauge and at a temperature between ambient temperature and the boiling point of the lowest boiling component of the reaction mixture.

18. Process according to claim 17 wherein the hydrogen pressure is between about 3.45 and 69 barg.

19. Process for the asymmetric hydrogenation of a β-hydroxycarbonyl compound to produce the corresponding 1,3-diol compound which comprises contacting the hydroxycarbonyl compound with hydrogen in the presence of a solution of a ruthenium complex compound defined in claim 1 in an inert organic solvent.

20. Process for the asymmetric hydrogenation of a β-hydroxycarbonyl compound containing from 4 to 20 carbon atoms to produce the corresponding 1,3-diol compound which comprises contacting the hydroxycarbonyl compound with hydrogen in the presence of a solution of a ruthenium complex compound defined in claim 2 in an inert organic solvent to form a reaction mixture, wherein the amount of ruthenium complex compound is about 0.00005 to 0.5 equivalents based on the β-hydroxycarbonyl reactant compound; and the process is carried out at hydrogen pressures of 0.07 to 137.9 bars gauge and at a temperature between ambient temperature and the boiling point of the lowest boiling component of the reaction mixture.

21. Process according to claim 20 wherein the hydrogen pressure is between about 3.45 and 69 barg.

* * * * *

UNITED STATES PATENT AND TRADEMARK OFFICE
CERTIFICATE OF CORRECTION

PATENT NO. : 6,939,981 B1
DATED : September 6, 2005
INVENTOR(S) : Boaz

It is certified that error appears in the above-identified patent and that said Letters Patent is hereby corrected as shown below:

Column 27,
Line 34, "VIIB,", first occurrence, should be -- VIB, --.

Column 28,
Line 47, "VIIB,", first occurrence, should be -- VIB, --.

Column 29,
Line 53, "VIIB,", first occurrence, should be -- VIB, --.

Column 30,
Line 3, "R2" should be -- $R^2$ --.

Signed and Sealed this

Sixth Day of December, 2005

JON W. DUDAS
*Director of the United States Patent and Trademark Office*